United States Patent
Moszner et al.

(10) Patent No.: US 8,889,758 B2
(45) Date of Patent: Nov. 18, 2014

(54) DENTAL MATERIALS CONTAINING HYDROPHOBIC NANOPARTICULATE SILICIC ACID CO-CONDENSATES AND USE THEREOF

(75) Inventors: Norbert Moszner, Triesen (LI); Volker Rheinberger, Vaduz (LI); Simone Klapdohr, Rosenheim (DE); Urs Karl Fischer, Arbon (CH)

(73) Assignee: Ivoclar Vivadent AG, Schaan (LI)

( * ) Notice: Subject to any disclaimer, the term of this patent is extended or adjusted under 35 U.S.C. 154(b) by 1041 days.

(21) Appl. No.: 12/226,129

(22) PCT Filed: Mar. 27, 2007

(86) PCT No.: PCT/EP2007/052892
§ 371 (c)(1),
(2), (4) Date: Oct. 7, 2008

(87) PCT Pub. No.: WO2007/115926
PCT Pub. Date: Oct. 18, 2007

(65) Prior Publication Data
US 2009/0043004 A1   Feb. 12, 2009

(30) Foreign Application Priority Data
Apr. 7, 2006 (DE) .......................... 10 2006 016 474

(51) Int. Cl.
| | | |
|---|---|---|
| C08F 283/12 | (2006.01) | |
| C08F 30/08 | (2006.01) | |
| A61K 6/083 | (2006.01) | |
| A61K 6/00 | (2006.01) | |
| C08G 77/12 | (2006.01) | |
| C08G 77/20 | (2006.01) | |

(52) U.S. Cl.
CPC .............. *A61K 6/0005* (2013.01); *A61K 6/0017* (2013.01); *A61K 6/083* (2013.01); *C08G 77/12* (2013.01); *C08G 77/20* (2013.01)
USPC .............................. 522/99; 523/105; 526/279

(58) Field of Classification Search
USPC ............................... 522/99; 526/279; 523/105
See application file for complete search history.

(56) References Cited

U.S. PATENT DOCUMENTS 5,112,884 A * 5/1992 Hanke ............................ 523/116
5,605,999 A * 2/1997 Chu et al. ......................... 528/24

FOREIGN PATENT DOCUMENTS

| DE | 39 03 407 | 8/1990 |
|---|---|---|
| DE | 198 16 148 | 10/1999 |
| DE | 198 34 990 | 4/2000 |
| DE | 199 03 177 | 7/2000 |
| DE | 199 10 895 | 9/2000 |
| DE | 694 25 473 | 11/2005 |
| EP | 0 451 709 | 10/1991 |
| EP | 0 804 919 | 11/1997 |
| EP | 0 618 242 | 7/1998 |

OTHER PUBLICATIONS

ORMOCER®, Information Sheet.*
M. A. Brook, Silicon in Organic, Organometallic, and Polymer Chemistry, HN Wiley & Sons, New York Etc. 2000, 312-314.
Stöber, Fink and Bohn (CF. J. Colloid Interface Sci. 26 (1968) 62-69.
Petroso et al. (Colloid Polymer Science 282 (2003) 19-26.
M. A. Brook, Silicon in Organic, Organometallic, and Polymer Chemistry, John Wiley & Sons, New York Etc. 2000, 320-324.
J. E. Mark, H. R. Allcock, R. West, Inorganic Polymers, Prentice Hall, Englewood Cliffs 1992, 141-145).
Encyclopedia of Polymer Science and Engineering, vol. 13, Wiley-Intersci. Pub., New York Etc. 1988, 754 FF.
J. P. Fouassier, J. F. Rabek (Ed.), Radiation Curing in Polymer Science and Technology, vol. II, Elsevier Applied Science, London and New York.

* cited by examiner

*Primary Examiner* — Melissa Rioja
*Assistant Examiner* — Jessica Roswell
(74) *Attorney, Agent, or Firm* — Ann M. Knab; Thad McMurray

(57) ABSTRACT

The present invention relates to dental materials comprising liquid, nanoparticulate functionalized hydrophobic co-condensates of tetraalkyl silicates with functionalized trialkoxysilanes of the formula I $$P-(CH_2)_n-Si(OR)_3$$

where P, R and n independently of one another have the following meanings:
P=a polymerizable $CH_2=CH-$, $CH_2=CH-O-$, styryl, (meth)acrylic or (meth)acrylamide group or an SH group capable of polyaddition,
R=methyl, ethyl or propyl and
n=from 3 to 15,
which can be prepared by co-condensation of tetraalkyl silicates with alkyltrialkoxysilanes functionalized in the ω position and subsequent end group functionalization with trimethylsilyl groups;
The invention further relates to the use of the dental materials for filling composites, fixing cements or materials for coatings.

25 Claims, No Drawings

DENTAL MATERIALS CONTAINING HYDROPHOBIC NANOPARTICULATE SILICIC ACID CO-CONDENSATES AND USE THEREOF

The present invention relates to dental materials comprising silicic acid ester co-condensates and their use.

Depending on the conditions chosen, i.e. as a function of the pH, the hydrolysis and condensation of tetraalkoxysilanes leads, as is known (cf. M. A. Brook, Silicon in Organic, Organometallic, and Polymer Chemistry, John Wiley & Sons, New York etc. 2000, 312-314), to a differing morphology of the products, which are constructed from "Q units" ($SiO_2$). Thus, under acidic conditions poorly branched polymer structures are formed, which can crosslink with a high conversion. As opposed to this, although under basic conditions the hydrolysis is slower, the accelerated condensation already leads initially to the formation of three-dimensional clusters and finally to dense $SiO_2$ particles. Correspondingly, according to Stöber, Fink and Bohn (cf. J. Colloid Interface Sci. 26 (1968) 62-69) monodisperse spherical $SiO_2$ particles in the range between 10 and 500 nm, "$SiO_2$ nanospheres", can specifically be prepared by hydrolytic condensation of tetraethyl silicate (TEOS) in a basic solution (ammonia) of water and alcohols. The particle size can be controlled here by the selection of the reaction conditions. Closely disperse small particles of, for example, about 5 to 8 nm in diameter have especially been obtained in a rapid reaction of TEOS in ethanol. According to Petroso et al. (Colloid Polymer Science 282 (2003) 19-26), $SiO_2$ nanospheres having a diameter in the range from 10-24 nm can be prepared by co-condensation of TEOS with methyltriethoxy silane (MTEOS) or dimethyldiethoxysilane (DMDEOS) and subsequent reaction with trimethylchlorosilane in n-hexane, which after their isolation as a powder can be completely dispersed in hexane, although they contain 19-40% of the silicon as $SiO_2$ structures. In the condensation of organically modified trialkoxy-silanes, highly viscous products are usually formed, which are designated as silsesquioxanes ($RSiO_{3/2}$, T structures) or alternatively as ormosils (organically modified silicates) and consist of more or less regularly constructed prismatic cage structures or ladder structures (cf. M. A. Brook, Silicon in Organic, Organometallic, and Polymer Chemistry, John Wiley & Sons, New York etc. 2000, 320-324). Typically low-viscosity polysiloxanes, such as, for example, poly-dimethylsiloxane, are prepared starting from di-functional silanes and are usually constructed from linear polymers having "D structures", $R_2SiO$ (cf. J. E. Mark, H. R. Allcock, R. West, Inorganic Polymers, Prentice Hall, Englewood Cliffs 1992, 141-145).

Acrylate-containing compositions comprising organopolysiloxane particles are known from DE 198 16 148 A1, the organopolysiloxane particles consisting of a single molecule. The particles have a mean diameter of 5 to 200 nm and are soluble at least to 5% by weight at 20° C. in a solvent (e.g. toluene, tetrahydrophoran or water). The compositions mentioned can be used in dental materials. It is the aim of DE 198 16 148 A1 to make available organopolysiloxane nanoparticles which can be used as a filler, that is as a solid component.

A process for the preparation of organopolysiloxanes containing organofunctional groups and organopoly-siloxanes prepared therefrom, organopolysiloxanes containing mercapto and alkoxy groups and processes for their preparation is known from DE 694 25 473 T3. The essential point here is that the silane hydrolysis and the polycondensation is carried out in the presence of a compound essentially containing neutral fluorine. Highly porous solids are formed in this hydrolysis and condensation.

DE 39 03 407 A1 describes a dental filling material which contains at least one polysiloxane or hetero-polysiloxane having polymerizable (meth)acrylic ester groups, which are accessible by condensation of tetra-alkyloxysilanes with tri- or dialkoxysilanes and/or titanium or zirconium tetraalkoxides. The materials described are solids which are used as fillers. The presence of nanoparticles or liquid compounds which are suitable as thinners is not described.

The invention is based on the object of making available dental materials which, in comparison to dental materials based purely on dimethacrylates, show approximately identical free-radical photo-polymerization reactivity and mechanical properties, but contain thinners having lower cytotoxicity, decreased solubility in water and a refractive index of less than 1.45.

This object is achieved by dental materials comprising liquid, nanoparticulate, functionalized hydrophobic co-condensates of silicic acid tetraesters with functionalized trialkoxysilanes of the formula I

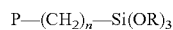

where P, R and n independently of one another have the following meanings:

P=a polymerizable $CH_2$=CH—, $CH_2$=CH—O—, styryl, (meth)acrylic or (meth)acrylamide group or an SH group capable of polyaddition, R=methyl, ethyl or propyl and n=from 3 to 15, which can be prepared by co-condensation of tetraalkyl silicates with alkyltrialkoxysilanes functionalized in the w position, i.e. in the end position.

Preferred trialkoxysilanes are those in which at least one of the variables of the formula (I) has the preferred definition described above.

Particularly preferred silanes according to the invention are those in which:

P=a polymerizable $CH_2$=CH—, (meth)acrylic or (meth) acrylamide group or an SH group capable of polyaddition, R=methyl or ethyl and n=from 3 to 10.

The co-condensates which are end group-functionalized with trimethylsilyl groups are preferable.

Suitable silylating agents in addition to trimethyl-chlorosilane are other known reagents for the introduction of the trimethylsilyl group, such as, for example, trimethylmethoxysilane, trimethylacetoxy-silane or hexamethyldisilazane. According to the invention, tetramethyl or -ethyl silicates are preferably employed as tetraalkyl silicates.

The condensation is preferably carried out under basic conditions. Ranges of the pH from 7.5 to 13 are particularly preferred, very particularly preferably from 7.5 to 11.

The hydrophobic silicic acid ester condensates are soluble in aliphatic alkanes; alkanes from $C_5$ to $C_{12}$ are in particular suitable. The condensates are particularly preferably soluble in hexane, heptane, octane or nonane. Condensates soluble in hexane are very particularly preferred.

The liquid, hexane-soluble, nanoparticulate, functionalized hydrophobic silicic acid co-condensates according to the invention can be prepared such that in the first step a hydrolytic condensation of TEOS or tetramethyl silicate (TMOS) or its mixtures is carried out with the trialkoxysilanes of the formula I or mixtures thereof in alcohol, preferably in ethanol or methanol at 30-80° C., preferably at 40 to 80° C., very particularly preferably at 50 to 60° C. using a catalyst, preferably an aqueous NH$_4$OH solution.

According to the invention, an amount of water of from 0.5 to 3.0 mol per alkoxysilane group (SiOR) is added. Amounts of water of from 2.0 to 3.0 mol per alkoxysilane group are particularly preferred.

The ratio of tetraalkyl silicate to trialkoxysilanes of the formula I can be varied. Preferably, it can be varied in the range from 0.5 to 1.2. Ranges from 0.5 to 1.0 are particularly preferred.

In the second step, the alcoholic solution of the hydrolytic condensate is then reacted with a solution of a silylating agent for the introduction of trimethylsilyl groups, preferably of trimethylchloro-silane (TMCS) in an aliphatic alkane, preferably alkanes from C$_5$ to C$_{12}$, particularly preferably hexane, heptane or nonane, over a period of from 10 to 40 h, preferably from 10 to 30 h, very particularly preferably from 10 to 20, where the amount of TMCS can vary in the range from 10 to 40 mol %, preferably 20 to 40 mol %, very particularly preferably 25 to 35 mol % of the amount of SiOR hydrolyzed in the first step. The liquid, nanoparticulate, preferably alkane-soluble, functionalized hydrophobic silicic acid co-condensates can be isolated by separating off the alcohol phase from the alkane phase, preferably the hexane phase additional extraction of the alcohol phase with alkane, preferably hexane, distilling off the solvent from the combined hexane phases and drying of the residue in a high vacuum. Here, the $^{29}$Si-NMR spectroscopic investigation of the liquid condensates formed has shown the presence of a considerable proportion of highly condensed Q structures (SiO$_2$ units), which verifies a nanoparticulate structure of the alkane-soluble, functionalized hydrophobic silicic acid co-condensates. The size of the particles varied in the range from 1 to 5 nm, the particle size determination being carried out by dynamic light scattering.

The dental materials according to the invention based on the liquid, nano-particulate, preferably alkane-soluble, functionalized hydrophobic silicic acid co-condensates can preferably be polymerized using the known free-radical initiators (cf. Encyclopedia of Polymer Science and Engineering, Vol. 13, Wiley-Intersci. Pub., New York etc. 1988, 754 ff.). Photoinitiators are particularly suitable (cf. J. P. Fouassier, J. F. Rabek (Ed.), Radiation Curing in Polymer Science and Technology, Vol. II, Elsevier Applied Science, London and New York 1993) for the UV or visible range, such as, for example: benzoin ethers, dialkylbenzil ketals, dialkoxyacetophenones, acyl- of the bisacylphosphine oxides, α-diketones such as 9,10-phenanthrenequinone, diacetyl, furil, anisil, 4,4'-dichlorobenzil and 4,4'-dialkoxybenzil and camphorquinone.

Furthermore, azo compounds, such as 2,2'-azobis(iso-butyronitrile) (AIBN) or azobis(4-cyanovaleric acid), or peroxides, such as dibenzoyl peroxide, dilauroyl peroxide, tert-butyl peroctoate, tert-butyl perbenzoate or di(tert-butyl) peroxide can also be used. Suitable initiators for heat-curing are also benzopinacol and 2,2'-dialkylbenzopinacols.

For the acceleration of the initiation of peroxides or α-diketones, combinations with aromatic amines can often also be preferred. Redox systems which have already proven suitable are: combinations of benzoyl peroxide or camphorquinone with amines, such as N,N-dimethyl-p-toluidine, N,N-dihydroxyethyl-p-toluidine, ethyl p-dimethylaminobenzoate or structurally related systems. Moreover, redox systems consisting of peroxides and reductants of this type, such as, for example, ascorbic acid, barbiturates or sulfinic acids, are also suitable.

The dental materials according to the invention can be employed as a mixture with conventional monomers polymerizable by free radicals, in particular with difunctional (meth)acrylate crosslinkers. In this regard, crosslinking bi- or multifunctional acrylates or methacrylates such as, for example, bisphenol A di(meth)acrylate, bis-GMA (an addition product of methacrylic acid and bisphenol A diglycidyl ether), UDMA (an addition product of 2-hydroxyethyl methacrylate and 2,2,4-trimethylhexamethylene diiso-cyanate), di-, tri- or tetraethylene glycol di(meth)acrylate, trimethylolpropane tri(meth)acrylate, pentaerythritol tetra(meth)acrylate, and butane diol di(meth)acrylate, 1,10-decanediol di(meth)acrylate, 1,12-dodecanediol di(meth)acrylate are especially suitable. Furthermore, comonomers which can also be used are particularly methacrylate-modified polysiloxane resins which are accessible by hydrolytic condensation of corresponding methacrylate group-containing silanes. These methacrylate-modified polysiloxane resins are distinguished by high functionality, since they usually carry, except for co-condensates with non-functionalized silanes, at least one polymerizable group per siloxane repeating unit. If silanes having two methacrylate groups are used as starting materials, each siloxane unit contains two polymerizable groups. The polysiloxanes are usually highly viscous and can accordingly be effectively diluted with the liquid, hexane-soluble, functionalized hydrophobic silicic acid co-condensates according to the invention. Analogously to the liquid, nanoparticulate, preferably alkane-soluble, functionalized hydrophobic silicic acid co-condensates according to the invention, polysiloxanes are also distinguished by a low solubility in water or aqueous solutions, so that even the smallest unpolymerized amounts of the dental material are not soluble under oral conditions and thus can also not be washed out. For the preparation of the polymerizable polysiloxane resins, suitable methacrylic silanes are commercially accessible, such as, for example, 3-(methacryloyloxy)propyltrimethoxysilane (MEMO), or can be prepared simply, for example, by reaction of glycerol dimethacrylate with 3-iso-cyanatopropyltriethoxysilane (DMAURS), EP 0 618 242 B1) or of glycerol dimethacrylate with glutaric anhydride and subsequently with 3-aminopropyltriethoxysilane (DMAGAMS,

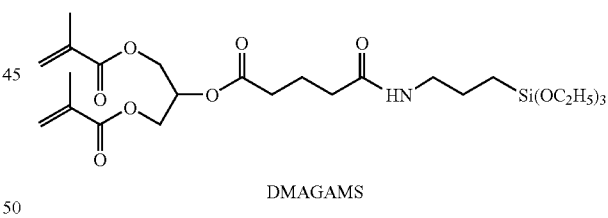

DMAGAMS

DE 199 03 177 C2), the preparation of the methacrylate-modified polysiloxane resins by hydrolytic condensation of the methacrylate group-containing silanes also being described in the patents indicated.

Di- or multifunctional acrylates can be employed as a reaction component for polyadditions with liquid, nanoparticulate, preferably alkane-soluble, SH-functionalized hydrophobic silicic acid co-condensates. Examples of suitable acrylates are ethylene glycol diacrylate, hexanediol diacrylate, tripropylene glycol diacrylate, ethoxylated bisphenol A diacrylate, polyethylene glycol 200 diacrylate, trimethylolpropane triacrylate and pentaerythritol tetraacrylate. Suitable catalysts employed for the polyaddition are preferably alkali metal hydroxides, such as, for example, KOH, tetraalkylammonium hydroxides, e.g. tetrabutylammonium hydroxide, in particular bicyclic amidines, such as 1,5-diazobicyclo[4.3.0]-

5-nonene or 1,8-diazobicyclo-[5.4.0]-7-undecene, and guanidines, especially tetra-methylguanidine.

Furthermore, the dental materials according to the invention based on liquid, nanoparticulate, preferably alkane-soluble, functionalized hydrophobic silicic acid co-condensates can be filled with organic or inorganic particles for improving the mechanical properties. Preferred inorganic fillers are amorphous spherical nanoparticulate fillers based on oxides, such as pyrogenic silicic acid or precipitation silicic acid, $ZrO_2$ and $TiO_2$ or mixed oxides of $SiO_2$, $ZrO_2$ and/or $TiO_2$ having a mean particle diameter of from 10 to 200 nm, microfine fillers and minifillers, such as quartz, glass ceramic or glass powder having an average particle size of from 0.2 to 5 µm and X-ray opaque fillers, such as ytterbium trifluoride or nanoparticulate tantalum(V) oxide or barium sulfate. Moreover, glass fibers, polyamide fibers or carbon fibers can also be employed.

Finally, if necessary further components such as, for example, stabilizers, UV absorbers, colorants or pigments and glidants can be added to the dental materials according to the invention based on liquid, nanoparticulate, preferably alkane-soluble, functionalized hydrophobic silicic acid co-condensates.

Dental materials, such as filling composites, fixing cements or materials for coatings can particularly be prepared based on the liquid, nanoparticulate, hexane-soluble, functionalized hydrophobic silicic acid co-condensates according to the invention. I.e., the dental materials according to the invention can be used for filling composites, fixing cements or materials for coatings. Materials of this type are distinguished by low water absorption, good mechanical properties, high resistance to abrasion and biocompatibility.

The trialkoxysilanes according to the invention are preferably employed for filling composites comprising a) 1 to 45% by weight, and particularly preferably 1.00 to 30% by weight, of hexane-soluble, nanoparticulate, functionalized, hydrophobic silicic acid co-condensates, b) 0.01 to 5% by weight, particularly preferably 0.1 to 2.0% by weight, of free radical initiator, c) 5 to 50% by weight and particularly preferably 0 to 40% by weight of other monomer components polymerizable by free radicals, d) 30 to 85% by weight and particularly preferably 40 to 80% by weight of a filler.

The dental materials according to the invention can furthermore be used for cements comprising:

a) 1 to 60% by weight, and particularly preferably 1.0 to 30% by weight, of hexane-soluble, nanoparticulate, functionalized, hydrophobic silicic acid co-condensates, b) 0.01 to 5% by weight, particularly preferably 0.1 to 2.0% by weight, of free radical initiator, c) 5 to 60% by weight and particularly preferably 0 to 40% by weight of other monomer components polymerizable by free radicals, d) 20 to 60% by weight and particularly preferably 30 to 60% by weight of a filler.

A further advantageous use of the dental materials according to the invention is coating materials comprising:

a) 1 to 95% by weight, and particularly preferably 10 to 40% by weight, of hexane-soluble, nanoparticulate, functionalized, hydrophobic silicic acid co-condensates, b) 0.01 to 5% by weight, particularly preferably 0.1 to 2.0% by weight, of free radical initiator, c) 5 to 60% by weight and particularly preferably 0 to 40% by weight of other monomer components polymerizable by free radicals, d) 0 to 20% by weight of a filler.

The invention is illustrated in more detail below by means of examples.

EXAMPLE 1

Synthesis of the Hexane-Soluble, Hydrophobic Silicic Acid Co-Condensate Functionalized with Methacrylate Groups McNano-1

0.06 mol of tetraethoxysilane (TEOS) and 0.06 mol of 3-methacryloxypropyltriethoxysilane are mixed with 150 ml of methanol and heated to 50° C. 1.116 mol (r=9.3 mol of $H_2O$/mole of Si) of a 0.1 N $NH_4OH$ solution are added to the mixture and it is stirred at 50° C. for 3 h. 0.134 mol of trimethylchlorosilane (TMCS) in 200 ml of n-hexane are subsequently added slowly at room temperature and the mixture is stirred for 18 h. The methanol phase is separated off and extracted with n-hexane, and the combined n-hexane phases are washed with water and dried over anhydrous sodium sulfate. After removal of the solvent on a rotary evaporator and drying at 40° C. ($10^{-1}$ mbar), 11.8 g (49.8% of theory) of a colorless, clear liquid are obtained. Characterization: $^1$H-NMR spectroscopy:ratio of methacrylate groups to trimethylsilyl groups=1:1.96; $^{29}$Si-NMR spectrum:ratio $R_3SiO_{0.5}$:$RSiO_{1.6}$:$SiO_2$=1:0.56:0.34; no monomers present; shear viscosity: 0.10 Pa·s; ignition residue: 36.9% by weight; elemental analysis: C content: 39.8% by weight; refractive index: 1.4346, particle size determination by dynamic light scattering by means of the Malvern Zeta Sizer Nano of a 1.0% strength ethanol solution of the condensate McNano-1 showed a mean particle size of 1.5 nm.

The example shows that despite the use of the mixture of the tetrafunctional TEOS and of the trifunctional 3-methacryloxypropyltriethoxysilane and basic condensation conditions a liquid, very low viscosity, nanoparticulate silicic acid co-condensate has formed.

EXAMPLE 2

Synthesis of the Silane Si-87 (1,3-di-methacryloyloxypropyl-[4-(3-triethoxy-silyl)propyl-N-methylaminocarbonyl)]-butyrate) and its Hydrolytic Condensation to the Resin OM-87

17.12 g (50 mmol) of 1,3-dimethacryloyloxypropyl-2-yl hydrogenglutarate (=1:1 reaction product of glycerol dimethacrylate with glutaric anhydride) are dissolved in 65 ml of dry methylene chloride, treated with 0.2 g of 4-dimethylaminopyridine and cooled to 0° C. 9.59 g (50 mmol) of N-(3-dimethylaminopropyl-N'-ethyl-carbodiimide hydrochloride are added to this in portions such that the temperature does not exceed 0° C. After warming to room temperature and stirring for 1 h, the reaction mixture is poured onto ice and the pH of the ice-cold mixture is adjusted to 6-7 using 0.3N hydrochloric acid. Subsequently, the methylene chloride phase is washed 3 times with 150 ml of ice water and dried over anhydrous sodium sulfate. After distilling off the solvent in vacuo, 21.9 g (80.8% of theory) of the silane Si-87 are obtained as a slightly yellowish, clear liquid.

For the hydrolytic condensation, 10.0 g of Si-87 are dissolved in 90 g of dry ethyl acetate. 1.04 g of an aqueous 1N $NH_4F$ solution are added to this and the solution is stirred at room temperature for 48 h. After filtration through a glass frit, the solution is stabilized with 0.5 mg of 2,6-di-tert-butyl-4-(dimethylaminomethyl)phenol and 1 mg of 2,6-di-tert-butyl-4-methylphenol. The slightly yellowish turbid solution is freed from the solvent at 40° C. on a rotary evaporator with introduction of air and subsequently dried in a fine vacuum at 40° C. and 0.06 mbar. 8.64 g (93.5% of theory) of the highly viscous ($\eta$=407 Pa·s) resin OM-87 are obtained.

EXAMPLE 3

Synthesis of a Hexane-Soluble Hydrophobic Silicic Acid Co-Condensate Functionalized with Mercapto Groups 0.06 mol of tetraethoxysilane and 0.06 mol of 3-mercaptopropyltriethoxysilane are mixed with 150 ml of methanol and heated to 50° C. 1.116 mol (r=9.3 mol of $H_2O$/mole of Si) of a 0.1N $NH_4OH$ solution are added to the mixture and it is stirred at 50° C. for 3 h. 0.134 mol of TMCS in 200 ml of n-hexane are subsequently added slowly at room temperature and the mixture is stirred for 18 h. The methanol phase is separated off and extracted with n-hexane, and the combined n-hexane phases are washed with water and dried over anhydrous sodium sulfate. After removal of the solvent on a rotary evaporator and drying at 40° C. ($10^{-1}$ mbar), a colorless, clear liquid (15.9 g (72.1% of theory)) is obtained.

Characterization: $^1$H-NMR spectrum:ratio of mercapto groups to trimethylsilyl groups=1:2.11; $^{29}$Si-NMR spectrum: ratio $R_3SiO_{0.5}$:$RSiO_{1.5}$:$SiO_2$=1:0.49:0.44; no monomers present; shear viscosity: 0.12 Pa·s; ignition residue: 38.6% by weight; refractive index: 1.4390.

EXAMPLE 4

Synthesis of the Hexane-Soluble, Hydrophobic Silicic Acid Co-Condensate Functionalized with Methacrylate Groups McNano-2 Starting from a Long-Chain Methacryloylsilane 0.03 mol of TEOS and 0.03 mol of 10-(methacryloxy)-decyltriethoxysilane are mixed with 75 ml of methanol and heated to 50° C. 0.56 mol (r=9.3 mol of $H_2O$/mole of Si) of a 0.1N $NH_4OH$ solution are added to the mixture and it is stirred at 50° C. for 3 h. 67 mmol of TMCS in 100 ml of n-hexane are subsequently added slowly at room temperature and the mixture is stirred for 17 h. The mixture is briefly filtered in order to remove some coarse solid particles. Subsequently, the methanol phase is separated off and extracted with n-hexane, and the combined n-hexane phases are washed with water and dried over anhydrous sodium sulfate. After removal of the solvent on a rotary evaporator and drying at 40° C. ($10^{-1}$ mbar), 11.7 g (77% of theory) of a colorless, clear liquid are obtained.

Characterization: $^1$H-NMR spectroscopy:ratio of methacrylate groups to trimethylsilyl groups=1:2.4; $^{29}$Si-NMR spectrum: degree of condensation of the T units: 83%; no monomers present; shear viscosity: 56 mPa·s; refractive index: 1.4332, particle size determination by dynamic light scattering by means of the Malvern Zeta Sizer Nano-S of a 1.0% strength ethanol solution of: the condensate McNano-2 showed a mean particle size of 3.7 nm.

The example shows that when using a long-chain hydrophobic silane the yield of liquid, very low viscosity, nanoparticulate silicic acid co-condensate resin markedly increases.

EXAMPLE 5

Preparation of a Composite using the Hydrophobic Silicic Acid Co-Condensate Functionalized with Methacrylate Groups McNano-1 from Example 1

Corresponding to Table 1 presented below, a composite based on A of a pure methacrylic trialkoxysilane poly-condensate OM-87 (from Example 2) and B with inclusion of the hydrophobic silicic acid co-condensate functionalized with methacrylate groups

TABLE 1

| Cement composition | | |
|---|---|---|
| Substances | Material A Amounts (% by wt) | Material B Amounts (% by wt) |
| OM-87 | 29.8 | 23.9 |
| McNano-1 | — | 5.9 |
| Photoinitiator[1] | 0.2 | 0.2 |
| Spharosil[2] | 12.3 | 12.3 |
| Glass filler 27884[3] | 44.1 | 44.1 |
| Aerosil OX-50[4] | 0.9 | 0.9 |
| Ytterbium trifluoride[5] | 12.7 | 12.7 |

[1] 1:1 mixture of camphorquinone and ethyl p-dimethyl-aminobenzoate
[2] $SiO_2$—$ZrO_2$ mixed oxide, 35% by weight of $ZrO_2$, particle size: 130-230 nm (Tokoyama Soda, Japan)
[3] Silanized barium aluminum borosilicate glass filler having a mean particle size of 1.2 μm (Schott, Landshut).
[4] Silanized pyrogenic silicic acid having a primary particle size of 40 nm (Degussa)
[5] $YbF_3$ having a particle size of 0.3-0.5 μm (Rhodia)

TABLE 2

| Composite characteristics | | |
|---|---|---|
| Material characteristic | Material A | Material B |
| Flexural strength (MPa) after 24 h | 62 | 74 |
| Flexural strength (MPa) after 24 h WS[1] | 51 | 75 |
| Flexural strength (MPa) after 7 d WS | 60 | 76 |
| Flexural E modulus (GPa) after 24 h | 5.84 | 5.25 |
| Flexural E modulus (GPa) after 24 h WS | 5.41 | 5.24 |
| Flexural E modulus (GPa) after 7 d WS | 6.16 | 5.95 |

[1] WS = water storage of the test articles at 37° C.

McNano-1 from Example 1 was prepared by means of an "Exakt" rolling mill (Exakt Apparatebau, Norderstedt). Appropriate test articles were prepared from the materials, which were irradiated for 2 times 3 minutes with a Spectramat dental light source (Ivoclar Vivadent AG) and were thereby cured. The flexural strength or the flexural E modulus was determined analogously to the ISO standard ISO-4049 (Dentistry—Polymer-based filling, restorative and luting materials).

It is evident from Table 2 that the material B leads to comparable mechanical characteristics in comparison to the material A. On account of the low viscosity of the McNano-1 silicic acid condensates, a higher degree of filling and thus a further improvement in the composite characteristics can be achieved.

The invention claimed is:

1. A method of restoring a tooth, comprising applying to the tooth a dental material as a filling composite, a fixing cement or a coating material, wherein the dental filling material comprises a liquid, functionalized hydrophobic co-condensate of tetraalkyl silicates with functionalized trialkoxysilanes of the formula I

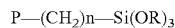

P—$(CH_2)$n—$Si(OR)_3$ where P, R and n independently of one another have the following meanings:
P=a polymerizable $CH_2=CH-$, $CH_2=CH-O-$, styryl, (meth)acrylic or (meth)acrylamide group or an SH group capable of polyaddition,
R=methyl, ethyl or propyl and
n=from 3 to 15,
prepared by co-condensation of tetraalkyl silicates with alkyltrialkoxysilanes functionalized in the ω position and subsequent end group functionalization with trimethylsilyl groups.

2. The method of restoring a tooth as claimed in claim 1, wherein the tetraalkyl silicates are tetramethyl silicate or ethyl silicate.

3. The method of restoring a tooth as claimed in claim 1, wherein the condensates are end group-functionalized with trimethylsilylating agent.

4. The method of restoring a tooth as claimed in claim 1, wherein the condensation is carried out under basic conditions.

5. The method of restoring a tooth as claimed in claim 1, wherein the functionalized hydrophobic co-condensates are soluble in hexane, heptane, octane or nonane.

6. The method of restoring a tooth as claimed in claim 1, wherein the trialkoxysilanes used are compounds of the formula

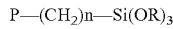

where P, R and n independently of one another have the following meanings:
P=a polymerizable CH2=CH—, (meth)acrylic or (meth)acrylamide group or an SH group capable of polyaddition,
R=methyl or ethyl and
n=from 3 to 10.

7. The method of restoring a tooth as claimed in claim 1 obtained in a 2-step process where
1) a hydrolytic condensation of tetraalkyl silicates with silanes is carried out with alcohol at 30 to 80° C. using a catalyst and
2) the alcoholic solution of the hydrolytic condensate is reacted with a solution of a trimethylsilylating agent over a period of from 10 to 40 hours.

8. The method of restoring a tooth as claimed in claim 7, wherein the alcohol is ethanol or methanol.

9. The method of restoring a tooth as claimed in claim 7, wherein in the first step the temperature is between 40° C. and 80° C.

10. The method of restoring a tooth as claimed in claim 7, wherein the catalyst is an $NH_4OH$ solution.

11. The method of restoring a tooth as claimed in claim 1, wherein water is added in an amount of from 0.5 to 2.0 mol per alkoxysilane group, the alkoxysilane group including both the functionalized trialkoxysilane of formula I and the tetraalkyl silicate.

12. The method of restoring a tooth as claimed in claim 1, wherein the ratio of tetraalkyl silicate to trialkoxysilanes of the formula 1 is between 0.5 to 1.2.

13. The method of restoring a tooth as claimed in claim 7, wherein the trimethylsilylating agent is trimethylchlorosilane.

14. The method of restoring a tooth as claimed in claim 13, wherein the trimethylchlorosilane is dissolved in alkane.

15. The method of restoring a tooth as claimed in claim 1, wherein 20 to 40 mol % of trimethyl-chlorosilane are employed, this information relating to the total amount of silanes hydrolysed in the first step.

16. The method of restoring a tooth as claimed in claim 1, wherein it contains initiators for the polymerization of the functionalized hydrophobic silicic acid co-condensates.

17. The method of restoring a tooth as claimed in claim 1, wherein it contains photoinitiators.

18. The method of restoring a tooth as claimed in claim 1, wherein it contains initiators for thermal curing.

19. The method of restoring a tooth as claimed in claim 1, wherein it contains monomers polymerizable by free radicals or polyaddition resins.

20. The method of restoring a tooth as claimed in claim 1, wherein it contains stabilizers, UV absorbers, colorants, pigments or glidants.

21. The method of restoring a tooth as claimed in claim 1, wherein it contains organic or inorganic filler particles.

22. The method of restoring a tooth as claimed in claim 21, wherein as inorganic fillers it contains amorphous spherical nanoparticulate fillers.

23. A method of restoring a tooth according to claim 1, comprising applying to the tooth the dental material as a filling composite further comprising
a) 1 to 45% by weight of hexane-soluble, nanoparticulate, functionalized, hydrophobic silicic acid co-condensates,
b) 0.01 to 5% by weight, of free radical initiator,
c) 5 to 50% by weight of other monomer components polymerizable by free radicals,
d) 30 to 85% by weight of a filler.

24. A method of restoring a tooth according to claim 1, comprising applying to the tooth the dental material as a cement further comprising
a) 1 to 60% by weight of hexane-soluble, nanoparticulate, functionalized, hydrophobic silicic acid co-condensates,
b) 0.01 to 5% by weight of free radical initiator,
c) 5 to 60% by weight of other monomer components polymerizable by free radicals,
d) 20 to 60% by weight of a filler.

25. A method of restoring a tooth according to claim 1, comprising applying to the tooth the dental material as a for coating material further comprising
a) 1 to 95% by weight of hexane-soluble, nanoparticulate, functionalized, hydrophobic silicic acid co-condensates,
b) 0.01 to 5% by weight, of free radical initiator,
c) 5 to 60% by weight of other monomer components polymerizable by free radicals,
d) 0 to 20% by weight of a filler.

* * * * *